(12) United States Patent
Diaz Carmena et al.

(10) Patent No.: US 10,842,449 B2
(45) Date of Patent: Nov. 24, 2020

(54) PORTABLE X-RAY DEVICE AND SYSTEM

(71) Applicant: SOCIEDAD ESPANOLA DE ELECTROMEDICINA Y CALIDAD, SA, Algete (ES)

(72) Inventors: Angel Diaz Carmena, Alcorcon (ES); Jose Garcia Perez, San Sebastian de los Reyes (ES); Ildefonso Moreno Vallejo, Rivasvaciamadrid (ES); Jesus Martinez Roca, Arroyomolinos (ES); Jacobo Pantoja Checa, San Sebastian de los Reyes (ES)

(73) Assignee: SOCIEDAD ESPANOLA DE ELECTROMEDICINA Y CALDID, SA, Algete (ES)

( * ) Notice: Subject to any disclaimer, the term of this patent is extended or adjusted under 35 U.S.C. 154(b) by 388 days.

(21) Appl. No.: 15/648,120

(22) Filed: Jul. 12, 2017

(65) Prior Publication Data
US 2019/0015057 A1    Jan. 17, 2019

(51) Int. Cl.
*A61B 6/00* (2006.01)
*A61B 6/06* (2006.01)

(52) U.S. Cl.
CPC .......... *A61B 6/4405* (2013.01); *A61B 6/4411* (2013.01); *A61B 6/508* (2013.01); *A61B 6/542* (2013.01); *A61B 6/56* (2013.01); *A61B 6/06* (2013.01); *A61B 6/4452* (2013.01); *A61B 6/548* (2013.01)

(58) Field of Classification Search
CPC ....... A61B 6/4405; A61B 6/508; A61B 6/542; A61B 6/56; A61B 6/4411; A61B 6/06; A61B 6/4452; A61B 6/548
See application file for complete search history.

(56) References Cited

U.S. PATENT DOCUMENTS

| | | | |
|---|---|---|---|
| 5,077,771 A | 12/1991 | Skillicorn et al. | |
| 2004/0120460 A1* | 6/2004 | Kuramoto | A61B 6/4233 378/102 |
| 2013/0136238 A1* | 5/2013 | Laws | A61B 6/08 378/147 |
| 2016/0206261 A1* | 7/2016 | Lan | A61B 6/462 |

(Continued)

FOREIGN PATENT DOCUMENTS

| | | |
|---|---|---|
| JP | 2016047308 A | 4/2016 |
| WO | WO 2016/208155 A1 | 12/2016 |

OTHER PUBLICATIONS

Rothmund, Windy, Handheld vs. conventional wall-mounted x-ray units, Aug. 1, 2019, RDH Magazine, pp. 1-16. (Year: 2019).*

(Continued)

*Primary Examiner* — Christine S. Kim
(74) *Attorney, Agent, or Firm* — Neal, Gerber & Eisenberg LLP; Bradley Rademaker; Nawshaba M. Siddiquee

(57) ABSTRACT

The present invention provides a portable x-ray device with a housing having a side and rear handle, each with triggers and indicator lights in locations suitable for manipulation for use. A trigger is located at each end of each handle and deposed at an angle to be actuated by an operator, with the triggers on one handle controlling a function of the device and the triggers of the other handle controlling a different function. The invention also provides a system including a device with a processor and a wireless device for communication with an external processor.

32 Claims, 8 Drawing Sheets

(56) References Cited

U.S. PATENT DOCUMENTS

2016/0209734 A1* 7/2016 Jackson ............... G03B 17/561
2018/0116623 A1* 5/2018 Inoue ....................... A61B 6/00

OTHER PUBLICATIONS

European Patent Office, International Search Report in International Application No. PCT/IB2018/055167 (dated Dec. 18, 2018).
European Patent Office, Written Opinion of the International Searching Authority in International Application No. PCT/IB2018/055167 (dated Dec. 18, 2018).
European Patent Office, Invitation to Pay Additional Fees and, Where Applicable, Protest Fee in International Application No. PCT/IB2018/055167 (dated Oct. 25, 2018).
Heska. Printed Oct. 11, 2017. https://www.heska.com/digital-imaging/equine-digital-x-ray/uno-6.aspx (2 pages).
Vetxray. Printed Oct. 11, 2017. http://vebcray.com/products/portable-x-ray-units/ (3 pages).

* cited by examiner

PORTABLE X-RAY DEVICE AND SYSTEM

BACKGROUND

X-ray devices used in medical and veterinary applications have several components which are often housed in separate housings or devices and electrically connected for function of the device. Such devices may be cumbersome and not well suited for use in remote locations or, in the case of portable x-ray devices, are bulky and difficult to hold in position and to manipulate to use the device in the proper position for use. Most often, such portable devices have no integral handle for holding the device, and instead rely upon attachment of a large u-shaped bracket which may be grasped by an operator for using and moving the device, or for attaching the device to a carrier or a boom arm for holding the device in position. Such devices, when equipped with a large handle that spans across the body of the device, are often difficult for a user to manipulate and to aim the front portion of the device for the x-ray function. These devices also are bulky for storage and transport, or may require the handle to me removed when the device is not in use.

Examples of such typical devices include the portable x-ray devices of companies marketed for veterinary and equestrian use by companies such as Sedecal (Spain), DRE Veterinary, Podoblock BV, Eickemeyer and others. Typically, these devices utilize a structure in which a separate control switch for activating the x-ray is tethered to a cable connected to the main housing of the device, thereby increasing the difficulty with manipulating the main body into position for aligning the x-ray field of exposure on the target while simultaneously activating the equipment for x-ray exposure with the tethered trigger mechanism, typically as a thumb-press switch connected to the main body by a cable. The difficulty of using this equipment for optimal alignment of the x-ray on the target is even greater when the operator of equipment attempts to limit the field of exposure such as with adjustment of a collimator light assembly associated with the device. Further, such devices utilizing a large attached handle assembly, such as a large u-shaped yoke which spans across the body of the device, cannot be easily and accurately aligned because the user has only one gripping location to hold and move the device, which is typically across a part of the device body that is not providing two-handed manipulation of the device alignment. Instead, the operator must hold the device with only one hand (at the large u-shaped handle) and uses the other hand to hold the tethered activation switch that is not integral with the device or the yoke-like handle. Further, when such commonly used devices are attached to a stand or boom support structure, the handle cannot be attached, creating another situation in which manipulation and alignment of the device for its intended use is difficult.

In light of these and other difficulties of typical portable x-ray devices, improvement is needed, and a more suitable structure and method of operation of x-ray devices are desired. The present invention represents an advancement of the structure and operation of x-ray devices, particularly for hand held and portable devices useful for veterinary and equestrian applications, or other applications in which portability is needed with optimal ease of use by a technician.

SUMMARY

The present invention relates to a portable x-ray device such as may be used for medical or veterinarian applications, and especially for equestrian x-ray diagnosis. According to an aspect of the present invention, a portable x-ray device has a housing with a side and a rear handle, each with triggers and indicator lights in locations suitable for manipulation by a user when holding the device in position and aiming the device for an x-ray. A trigger is located at each end of each handle, positioned on a platform that is deposed at an angle relative the handle and the housing, in position to be manipulated by an operator, and wherein the triggers on one handle may be activated for a function of the device, and the triggers of the other handle may be activated for a different function of the device. the invention also provides for a system for use of a portable x-ray device, including a device with inner components and a processor, a wireless communication device for electrical signal between the processor and an operator's computer, wherein the processor is in communication with a remote computer through communication with the operator's computer.

More specifically, the present invention concerns a portable x-ray device comprising a housing having a housing wall arrangement defining an interior space, an x-ray generator and an x-ray tube encased by the housing within the interior space. The housing has a side wall defined by a portion of the housing wall arrangement and a rear wall defined by a rear portion of the hosing wall arrangement. A side handle, with a first end integral with the side watt and a second end integral with the side wall, has a first gripping portion that resides between the first and second end of the side handle. A rear handle, with a first end that is integral with the rear wall and a second end integral with the rear wall, has a second gripping portion that resides between the first and second end of the rear handle. A first actuator trigger is positioned on each end of the side and rear handle, the actuator trigger is positioned adjacent the gripping portions of the handles and is configured to control a radiological function of the device. The actuator triggers are each preferably located on a platform of the handle which has an angular displacement for positioning the trigger in a manner suitable for an operator to depress the trigger with his or her thumb. In a preferred for of the invention, the housing has an indented region defining a void region adjacent the side handle to provide a space for a user to fit a hand to hold the side handle. The rear handle is preferably aligned along the central area of the end of the device housing, and has a gripping portion that is spaced from the rear wall of the device, providing a space for a user to hold the rear handle.

The present invention provides a system for a portable x-ray device that includes a housing with an interior space holding a processor and x-ray components. The processor is in electrical communication with at least one x-ray component and with a wireless communication device associated with the device, preferably a separate operator's computer generally located at or very near the location of the portable device. The operator's computer is in wireless communication with the device and with a remote communication device configured to receive signal from the operator computer. The signal received at the remote location is generated by the portable x-ray device and relayed through the operator computer, and signal that is generated by a remote-location processor is relayed through the operator's computer to the device. In an embodiment of this system, the operator computer provides a communicative link between the processor within the hand-held x-ray device and the processor of a remote computer, providing a communication link between the remote location processor and the x-ray device, including commands delivered to the x-ray device processor to alter one or more parameters of the device, such adjustment of a parameter of the x-ray generator.

A better understanding of the invention will be obtained from the following detailed descriptions and accompanying drawings, which set forth illustrative embodiments indicative of the various ways in which the principals of the invention may be employed.

Figure 1:
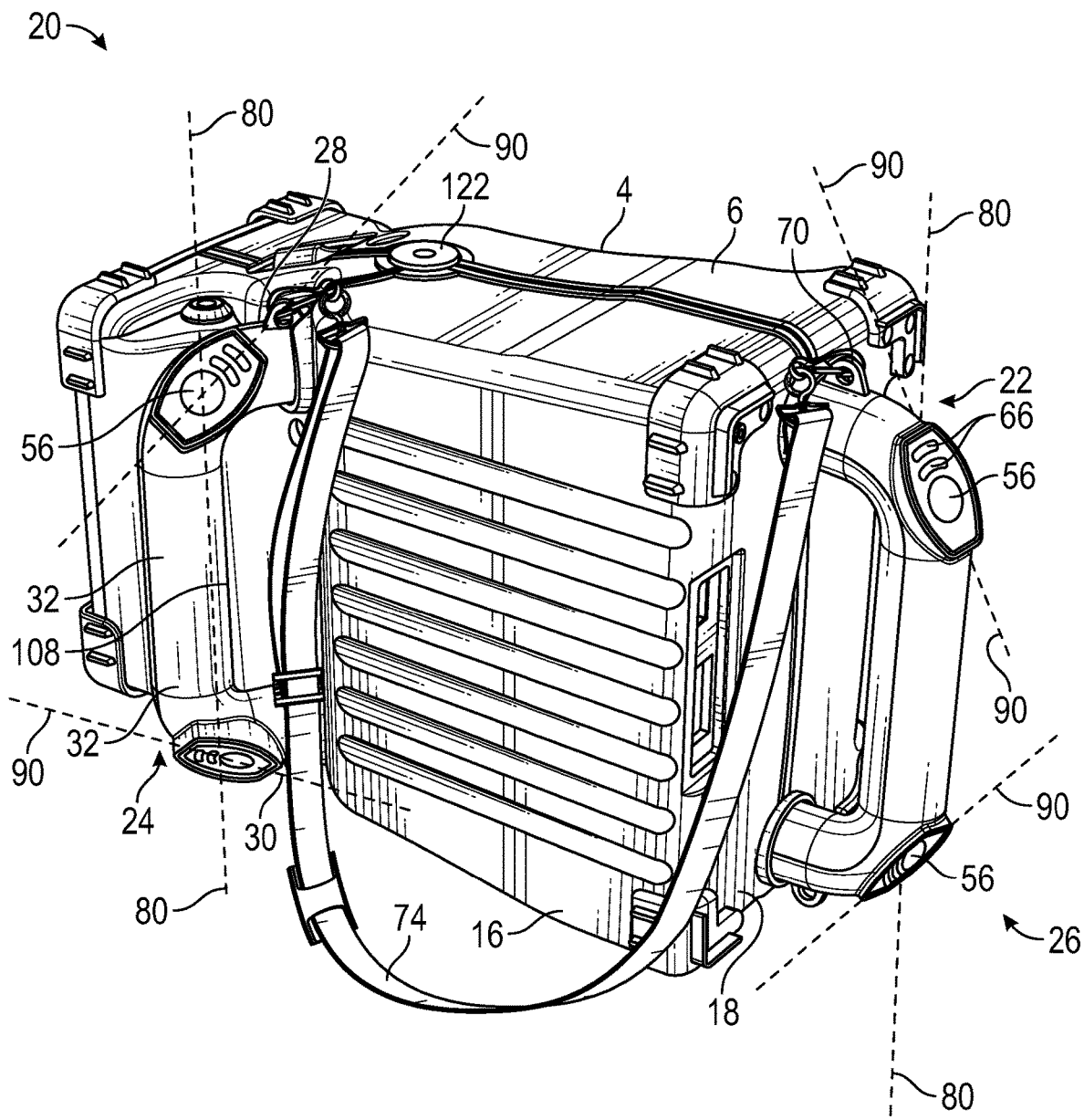
FIG. 1 is an elevated perspective view of a portable x-ray device according to an embodiment of the present invention, showing a main body with a side handle assembly and a rear handle assembly.

Illustrative and exemplary embodiments of the invention are described in further detail below with reference to and in conjunction with the figures.

DETAILED DESCRIPTION

The description that follows describes, illustrates and exemplifies one or more embodiments of the invention in accordance with its principles. This description is not provided to limit the invention to the embodiment(s) described herein, but rather to explain and teach the principles of the invention in order to enable one of ordinary skill in the art to understand these principles and, with that understanding, be able to apply them to practice not only the embodiment(s) described herein, but also any other embodiment that may come to mind in accordance with these principles. The scope of the invention is intended to cover all such embodiments that may fall within the scope of the appended Claims, either literally or under the doctrine of equivalents.

It should be noted that in the description and drawings, like or substantially similar elements may be labeled with the same reference numerals. However, sometimes these elements may be labeled with differing numbers or serial numbers in cases where such labeling facilitates a more clear description. Additionally, the drawings set forth herein are not necessarily drawn to scale, and in some instances proportions may have been exaggerated to more clearly depict certain features. As stated above, this specification is intended to be taken as a whole and interpreted in accordance with the principles of the invention as taught herein and understood by one of ordinary skill in the art.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects.

FIG. 1 depicts a portable x-ray device 2 according to an embodiment of the invention, in which the device 2 has a housing 4 with a housing wall arrangement 6 defining an interior space. Within the interior space 8 of the housing resides working components 10 of the device 2, including an x-ray generator 12 and an x-ray tube 14, and which also include light emitting targeting components. In a preferred embodiment, the housing 4 is defined by a watt structure, including a side wall defined by a portion of the housing wall arrangement 6 and a rear wall 18 defined by a rear portion of the hosing wall arrangement 6. Further, in the preferred embodiment, the housing wall arrangement 6 forms a housing that has an overall single interior space 8 that holds the functional components 10 of the x-ray device 2, such that the housing 4 is preferably formed as an overall uni-body construction rather than separate housings of components secured together. In this aspect of the embodiment shown, the outside dimensions of the housing 4 may be formed in a general forward wedge shape to facilitate the user having a directional aim of the device 2 as the user is positioned at the rear of the device 2 and is holding the device, while directing the aim of the x-ray toward a target. This aspect of the embodiment shown in the Figures, such as in FIG. 5 which shows a smaller front end 20 relative the rear end 22 of the device housing 4, provides enhanced ability for a user to aim the device 2 while free-hand holding the device 2 and initiating the functions of the device 2 by activating a trigger as described herein.

The device 2 of the present invention includes a side handle 24 and a rear handle 26. The side handle 24 preferably has a first end 28 and a second end 30 which are integral with the side wall, and a gripping portion 32 of the side handle 24 resides between the first and second ends (28, 30). This provides a first gripping portion 32 for a user to grip the handle 24 adjacent the side of the device 2, that is, adjacent the side wall 16, preferably at a suitable close distance away from the side wall of the device 2 to facilitate accuracy of a user aiming the device 2. In the preferred embodiment shown in the Figures, the side handle 24 is a generally U-shaped handle, with each end of the U-shape being integrally secured or otherwise formed with the housing 4, such that the gripping portion of the side handle 24 is locate in the range of less than about 4 inches (less than about 10 cm) from the side wall of the housing 4. In a preferred embodiment, as shown in the Figures, the side wall 16 of the housing 4 includes a recessed region 34 adjacent the side handle 24, providing a void area 36 configured for providing space for the user to place a hand hold onto the side handle 24 gripping portion 32. As shown in FIGS. 1-4 and 8-9, the recess 34 in the side of the device 2 is an inward depression, preferably formed of curved recessed of an extent of the characteristic plane 38 of the side wall 16 i.e., the recess 34 is formed by an inwardly directed area of the sidewall 16 of the housing 4 at a location between the front end 20 and rear end 22 of the device 2. The recess 34 is located in a forward portion of the device 2, between the mid-line 40 and the front (or proximal) 20 end of the device 2. This arrangement provides a preferred location for the void area 36 adjacent the side handle 24, located in the front portion of the length of the housing 4. The gripping portion 32 of the side handle 24, residing adjacent the recess 34, is also located in the front portion of the length of the housing 4 (also at a location between the mid-line 40 and the proximal (front) end 22). The position of the side handle 24 and the adjacent void area 36 in the front half of the length of the housing 4 provides an accessible gripping portion 32 at a beneficial location for an operator of the device 2 to manipulate the device for alignment of the x-ray.

The rear handle 26, positioned at the rear end 22 (the distal end) of the housing 4, is a handle 26 formed of a first end 42 and a second end 44, preferably with at least the first end 42 being integral the rear wall 18. The rear handle 26 has a gripping portion 46 between its first end 42 and the second end 44, wherein the gripping portion 46 is located an extent away from the rear wall 18. In the embodiment shown in the Figures, the rear handle 26 has at least a portion formed as a generally U-shaped body, with each end (42, 44) of the rear handle 26 is integrally attached to the rear portion 22 of the device 2, shown as having both ends (42, 44) of the handle 26 secured to the rear wall 18 of the device 2. In alternate embodiments, the side handle 24 and rear handle 26 may each be formed as a generally L-shaped body, with one end secured integral with the walls (16, 18) and the gripping portion (32, 46) of each handle (24, 26) thus spaced a distance from the walls (16, 18) to provide void regions (36, 48) between the gripping portions (32, 46) and the wall of the housing 4. This arrangement provides void regions (36, 48) for a user to place a hand for holding each handle (24, 26). Further, in alternate embodiments the rear wall 18 may include a recess portion to provide all or part of the void area 48 adjacent the rear handle 26 gripping portion 46, similar to that of the side handle 24, while keeping with a main objective of the invention.

According to an aspect of the invention, the handles are in locations to facilitate the user's ability to manipulate the proximal 20 and distal 22 ends relative one another to aim the device 2 when in use. In the preferred embodiment shown in the Figures, the structure of a side handle 24 in the front portion 50 of the length of the device 2, and a rear handle 26 with a gripping potion located at a distance from the rear wall 18, together provide gripping areas (32, 46) for the user to grip the device 2 on either side of the mid-line 40, thus providing gripping locations at each side of a fulcrum point 52, generally at the center of gravity of the device in the middle region 54 of the housing 4. This aspect of the invention, as shown in FIGS. 3-4 and 8-9, provides a desirable relative distance for the parts of the assembly of the device 2, wherein a first handle 24 is located in the front portion 50 and a second handle 26 is located a distance away 102 at the rear 22 of the device 2, with a fulcrum 52 between the two handles being in the middle region 54 of the device 2 to allow the user to tilt the device 2 for alignment for directing the x-ray on a target. The structure of the invention provides such hand gripping areas (32, 46) on either side of a central fulcrum 52 regardless of whether the device 2 is held with the first handle is located on the top (FIGS. 3-4) or if held such that the first handle is positioned along the side (such as in FIGS. 8-9).

A significant aspect of the invention provides access for a user to activate functional components 10 of the x-ray device 2 while holding and manipulating the device 2 in the desired alignment for x-ray exposure. This is provided by at least one activation trigger 56 located adjacent the gripping portion (32, 46) of at least one handle, and preferably both handles. In the preferred embodiment, an actuator trigger 56 is positioned on each side of the gripping portion of the side handle 24 and on each side of the gripping portion 46 of the rear handle 26. Each trigger 56 is configured to control an aspect of a radiological function of the device 2. The function controlled by one trigger 56 may include one or more of the typical functions of such an x-ray device 2, such as (a) activation of an collimator light 62 to generate light emitted from the front/proximal end 22 for illuminating the target field of the intended x-ray exposure, (b) activation of a laser 64 to generate a laser emitted from the front end 22, (c) activation of the x-ray exposure itself by turning on the x-ray generator 12 and/or function of the x-ray tube 14. In a preferred embodiment, each trigger 56 may be a button-type trigger mechanism, adapted to provide multiple stages for depressing the button to activate different functions of the device 2 in sequence. For example, in a preferred embodiment, a button-type trigger 56 is positioned adjacent a handle gripping portion, positioned to be manipulated/activated by a user's thumb wherein the trigger is configured to be pushed to a first level to activate a collimator light 62 to illuminate the target area and a second level for activating the laser light 64 emitting from the front end 22 to provide a target of the x-ray area. An alternative trigger structure positioned adjacent a gripping area of a handle for manipulation by a user's thumb may be for activating the x-ray functions, such that a trigger is configured to be pressed a first position to provide indication of a readiness state of the x-ray generator 12 and then may be pressed to a second position to activate x-ray exposure.

Figure 8:
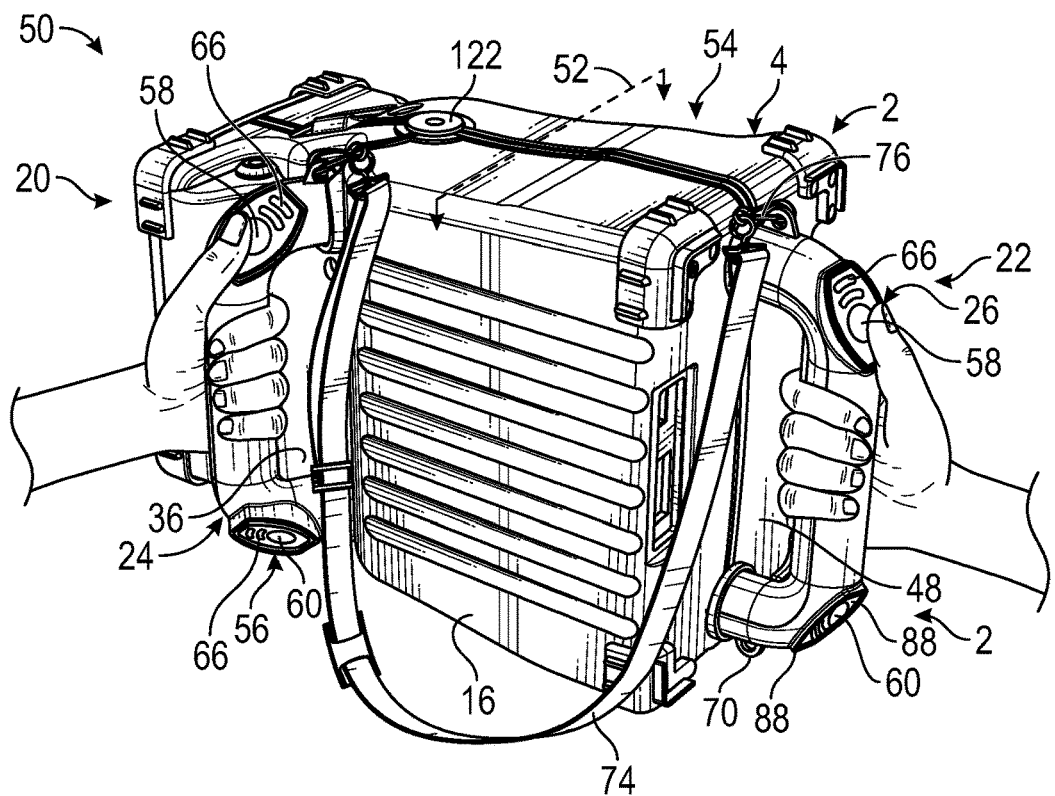
FIG. 8 is an elevated perspective view similar to the view of FIG. 1, showing operation of the device by an operator gripping the side handle assembly with the operator's left hand and gripping the rear handle assembly with the operator's right hand, and a strap connected to extend above the device housing.
Figure 9:
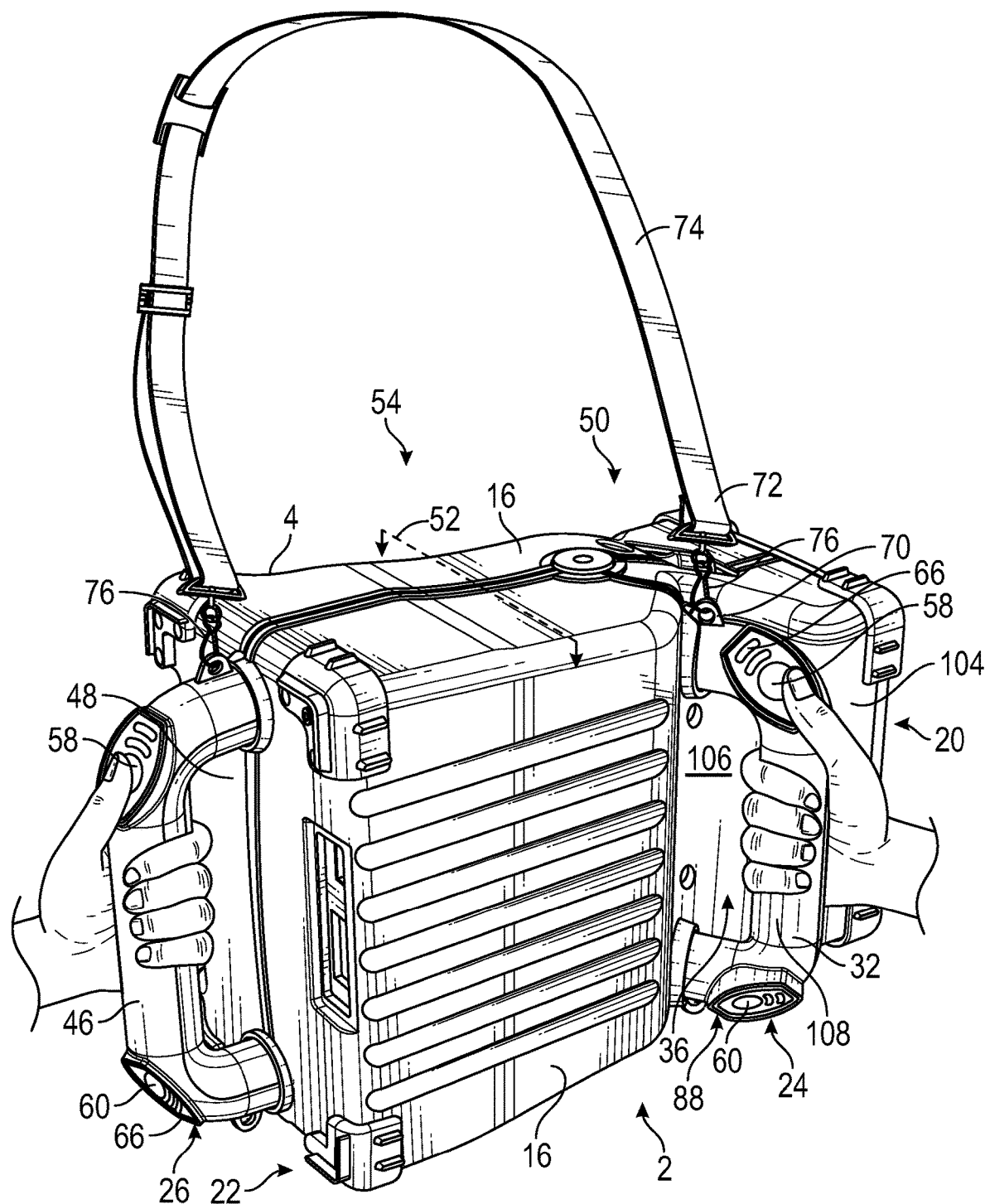
FIG. 9 is an elevated perspective view of the device rotated 180 degrees from the position in FIG. 8, showing use of the device by with an operator gripping the side handle assembly with the operator's right hand and gripping the rear handle assembly with the operator's left hand, and a strap connected to extend above the device housing.

In the embodiment shown, a first actuator trigger 56 is positioned adjacent the first end of a handle and a second actuator trigger 60 is positioned adjacent the second end of the handle providing a trigger located on each side of the gripping portion of the handle wherein each such trigger on the handle is configured to activate the same functions of the device 2. Because each trigger 56 of a particular handle (either the side handle 24 or the rear handle 26) is preferably configured to activate the same function of the device 2, such that the user may activate the function of working components 10 regardless of holding the handle with the right or left hand (FIGS. 8 and 9). Thus, in the preferred embodiment of the invention, each handle (the side and rear handle) has a pair of triggers 56, each located adjacent an end (28, 30) (42, 44) of the handle 24, 26, to provide activation of multiple functions by the user as the user holds the device 2 at the gripping portions 32, 46 of the handles 24, 26. In the preferred embodiment, the triggers 56 of the side handle 24, located on each side of the gripping portion 32 to be activated while gripped by the user's right or left hand, are configured to control functions for defining the target for x-ray exposure—the collimator light and the laser emitting assemblies. Likewise, in this embodiment, the triggers located on each side of the gripping portion 46 of the rear handle 26 each are configured to activate functions associated with initiating the x-ray exposure, such as the functions of the working components 10 identified above (identifying the readiness state of the device 2, and to activate x-ray exposure by the generator 12 and x-ray tube 14 through signal to the processor 134). In this manner, the device 2 has a first and second actuator trigger positioned on each side of the gripping portion 46 of the rear handle 26, each configured to control a first function of the device 2, and another pair of actuator triggers positioned adjacent the ends of the side handle 24 gripping portion 32, each configured to control a second function of the device 2.

Figure 11:
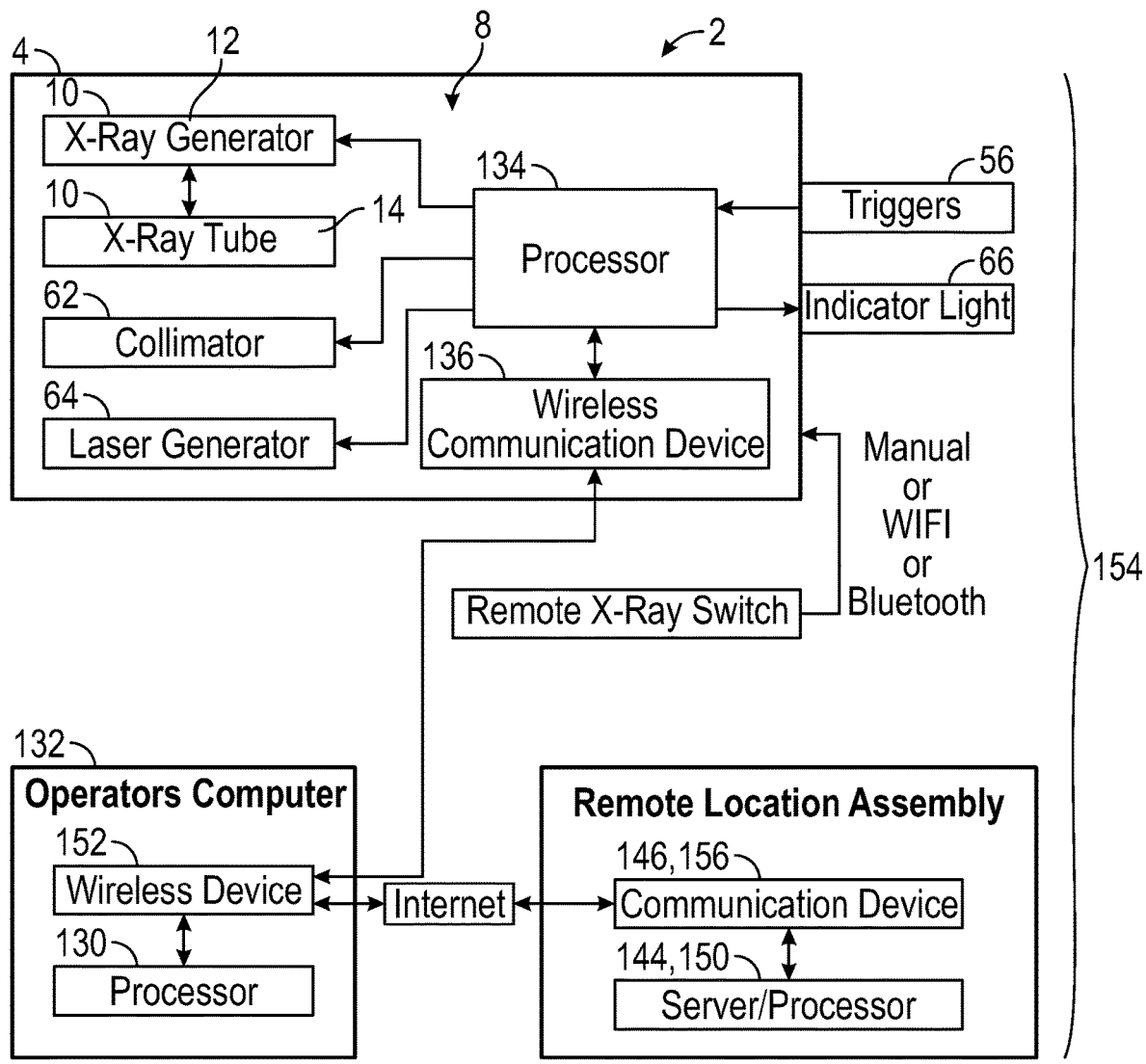

More specifically, the pair of triggers (58, 60) located at the rear handle 26 are configured with electrical connection to control activation of x-ray exposure (i.e., the x-ray actuator trigger), by initiating a signal for activating function of the generator 12 and resulting activation of the x-ray tube 14. The pair of triggers (58, 60) located at the side handle 24 are configured with electrical connection to control activation of targeting components at the front end 20, including a collimator light 62 and a laser 64 (i.e., the targeting trigger). Indicator lights 66 located adjacent each trigger 56 are configured to provide indication of the readiness and/or activation of these described functions of the device 2. Each indicator light 66 is configured to provide indication of the readiness and/or activation of at least one function associated with the immediately adjacent trigger 56. As shown in FIG. 11, a central processor 134 is electrically connected to each trigger 56 and indicator light 66, an electrical connection configured to receive signal by the processor from the triggers 56 and to deliver signal to the indicator lights 66.

Each actuator trigger (58, 60) located on the handles (24, 26) is preferably a button-type trigger 56 that may be depressed by the user's thumb to varying levels as described above. This positioning is shown in FIGS. 8 and 9, wherein the user may hold the a side handle 24 with his or her left hand (FIG. 8) or right hand (FIG. 9), while always having a trigger located adjacent the thumb area of the gripping portion 32 for activating functions of the device 2. The user may then also hold the rear handle 26 with the other hand, and an actuator trigger 58, 60 is located adjacent the thumb area of the gripping portion 46 for activation of functions of the device 2. Indicator lights 66 are located adjacent each trigger 58, 60 for the operator to receive information relating to the function(s) associated with the adjacent trigger. The indicator lights 66 are configured to be in electrical communication with the processor as described, and optionally may be in electrical communication with an internal component within the housing 4 to receive direct indication of the readiness or activation of the component.

Figure 3:
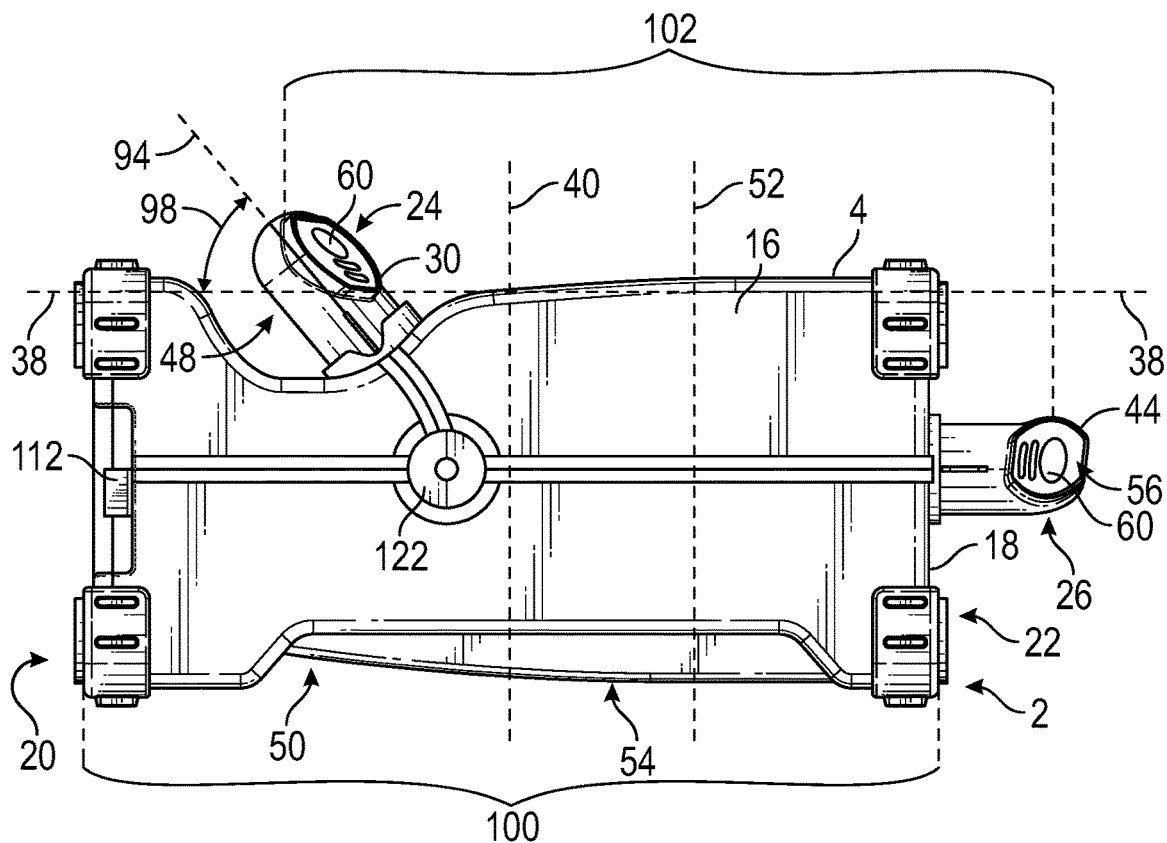
FIG. 3 is an underside view of the embodiment of the invention shown in FIG. 1.
Figure 4:
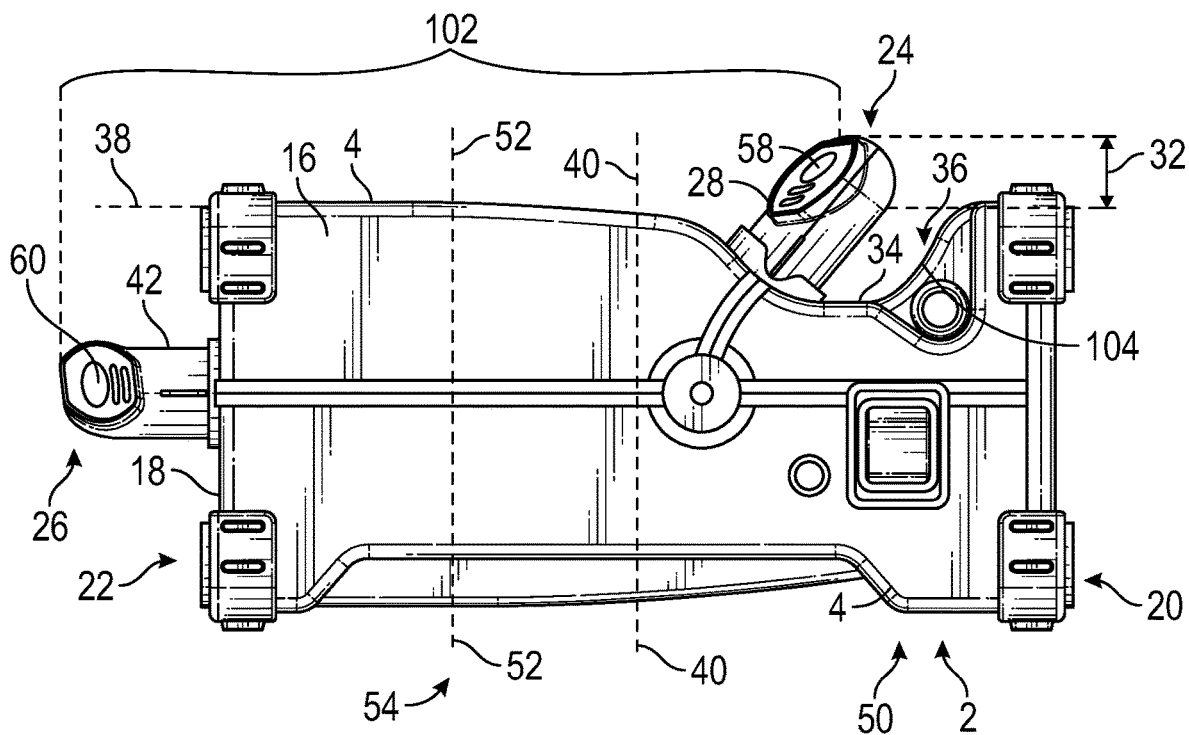
FIG. 4 is a topside view, opposite the view of FIG. 3, of the embodiment of the invention shown in FIG. 1.

The structure described above and shown in the Figures is preferable for providing a suitable trigger location for holding the device 2 in other orientations than what is shown in FIGS. 8 and 9, including arrangements in which the device 2 is manipulated to be held with the side handle 24 in the upper or top of the device 2, such as shown in FIGS. 3 and 4. And, regardless of the position of the device 2 by the operator/user, an activation trigger is in a suitable position to be pressed by the operator's thumb, while an indicator light 66 adjacent that trigger 56 is in a location that may be viewed by the operator.

Strap connectors 70 are also preferably provided adjacent at least one end of the handles (24, 26), thus providing a connection for an end 72 of a strap 74 at each handle 24, 26 regardless of the positioning of the device 2. In this embodiment, a strap 74 is located at an upper side of the device 2 for holding the device 2 in position, regardless of whether it is positioned as shown in FIG. 8 (right-handed use of the main actuation trigger of the rear handle 26), or positioned as shown in FIG. 9 (left-handed use of the main actuation trigger on the rear handle 26). In the preferred embodiment, a connector 76, such as a loop or similar receiver such as shown in the Figures, is provided to receive a mating loop, latch or projection to secure the end 72 of the strap 74 to the connector 70. Alternative means for securing the strap 74 with a connector 70 may be used, such as mating buckles, screw-type fasteners, socket connectors or other such mating parts that provide frictional engagement for securing an end 72 of the strap 74 to the device 2 adjacent ends of the handles.

The use of a strap 74 connected in such locations, i.e., at connectors 70 located adjacent (and preferably directly at) each of the two handles, facilitates support and positioning of the device 2 by the user. The handles (24, 26) are each located adjacent the proximal end 20 and distal end 22 respectively, with the fulcrum 52 of balanced movement being located between the two handles in the central region 54 of the housing 4. This provides stability When moving the x-ray device 2 to align the target field of the exposure and then activating the x-ray exposure, which is done while holding the device 2 in the user's hands. Optimally, this structure provides attachment of a strap 74 at the top of the device 2 regardless of alternate positioning of the device 2 (FIGS. 8 and 9) because a connector 70 is located at each end (28, 30) of the side handle 24, and at each end (42, 44) of the rear handle (26).

Figure 2:
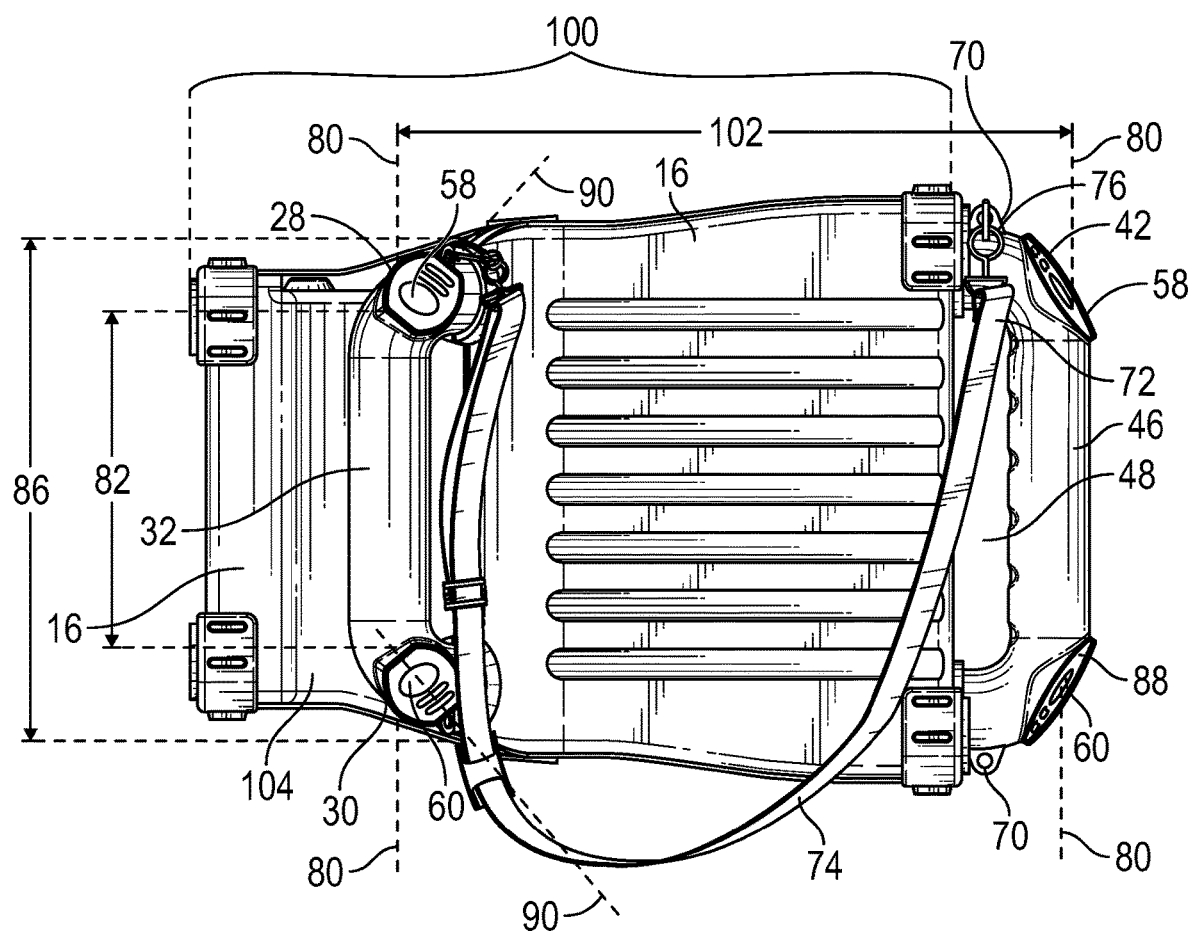
FIG. 2 is a side view of the embodiment of the invention shown in FIG. 1.

It is also an aspect of the preferred embodiment for the side and rear handle (24, 26) to each be arranged in a particular manner to one another. Each handle has a central axis 80 residing along the length 82 of the gripping portion, wherein the central axis 80 of the side handle 24 is generally parallel the axis 80 of the rear handle 26. In the preferred embodiment, as shown in the Figures, the alignment of the elongated length 82 of the gripping portions (32, 46) of the side and rear handle (24, 26) are generally along parallel paths, such as shown in FIGS. 1 and 2. This arrangement provides a suitable relative alignment of the gripping portions of the two handles for a user to comfortably grip the device 2 with two hands (each at one of the handles) for manipulating the position of the device 2 for aiming the x-ray field on a target area.

The position of the triggers 56 is an important aspect of the invention, to provide suitable location for a user to activate functional components 10 of the device 2 while holding the device 2 in each hand. As indicated and as shown in the Figures, the triggers 56 are preferably located adjacent each end of the gripping portions (32, 46) of the side and rear handles (24, 26). In the preferred form of the invention, the triggers 56 are each located on a respective platform 88 on the handle adjacent the gripping portion (32, 46), near the ends (28, 30) of the particular handle. As shown in FIGS. 1, 2 and 8-9, the platforms 88 preferably have an elongated extent with an axis 90 that is generally transverse to the axis 80 of the length of the handle gripping portion. In the preferred embodiment, each trigger platform has an axis 90 which extends at an oblique angle relative the axis 80 of the elongated gripping portion of the handle body. This provides a trigger platform 88 (a base for the trigger) residing along a plane that is offset from the central axis 80 of the handle—i.e., adjacent to the gripping portion and which is angularly displaced from the axis of elongated gripping portion of the handle—thus in an optimal position for a user to activate the trigger with the user's thumb while holding the gripping portion 32, 46 of the handles 24, 26. This arrangement also provides a trigger 56 which is activated by pressing the trigger in the directional path natural for the user—i.e., the user pressing his or her thumb on the trigger in a direction transverse to the axis of the handle. Because the side handle 24 spans across a major extent of the side wall of the housing 4, this embodiment provides a trigger 56 on a trigger platform 88 located adjacent each end of the extent of the side wall 16, or sidewall height, and the strap connector is also provided at each such end of the sidewall height. Similarly, because this embodiment is configured to provide a handle gripping portion 46 that extends across a major extent of the rear wall height, a trigger is located on a trigger platform positioned adjacent each end of the rear wall 18 height, and a strap connector 70 is also provided at each end of the rear wall 18 height. Thus, the device 2 may be manipulated to be flipped over 90 degrees (turning the side to be a top—see FIG. 3-4 and 7) or 180 degrees (flipping the end of the rear handle 26 which is on top— compare FIGS. 8 and 9). While the device is alternatively oriented in each of these positions, a trigger 56 is located adjacent the gripping portion (32, 46) for manipulation by the user's thumb.

Figure 7:
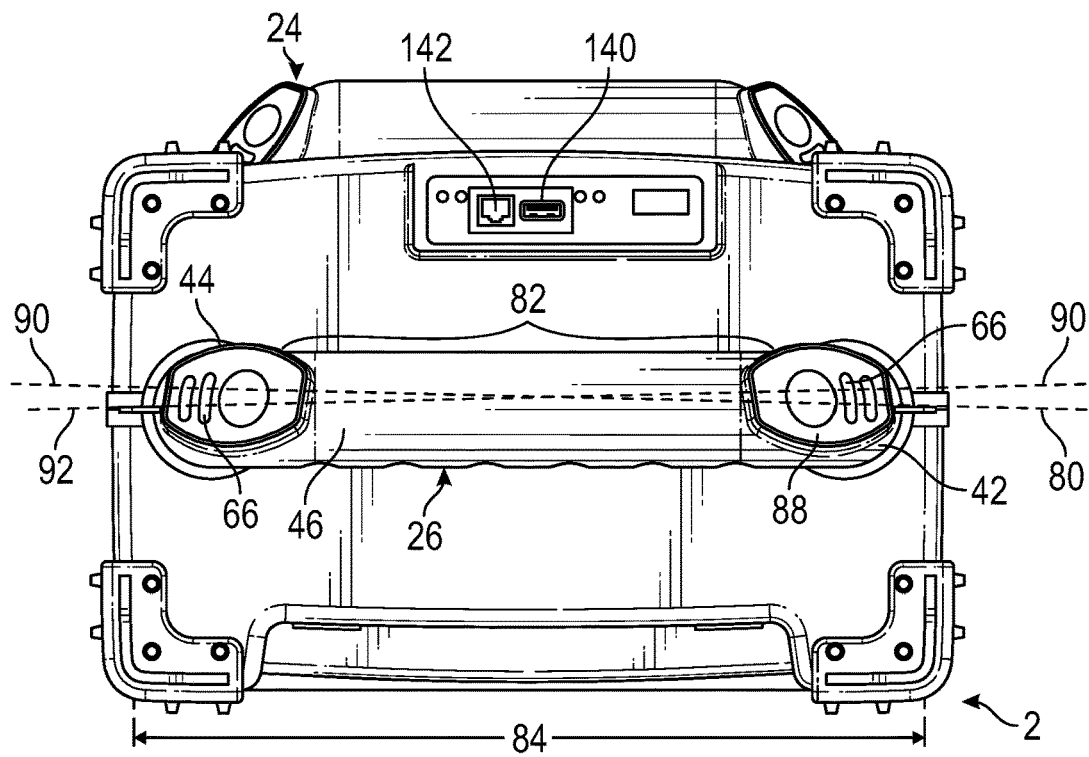
FIG. 7 is a rear view of the device shown in FIG. 1.

As is shown in FIG. 7, the rear handle 26 preferably is aligned such that the axis 80 of the elongated length 82 of the gripping portion 46 generally resides along a central area of the rear wall 18. In the embodiment shown (FIG. 7), the elongated length 82 of the rear handle 26 extends generally along the central portion, or median line, 92 of the rear wall 18, which defines the characteristic height 84 of the rear wall 18 when held in operating position such as in FIGS. 8 and 9. This provides a preferred location for the gripping portion of the rear handle 26 at the middle of the rear wall 18 such that the device 2 may be gripped and manipulated comfortably regardless of whether the device 2 is flipped to have the side handle 24 on the right (FIG. 9) or the left (FIG. 8). Further, in the preferred embodiment, as shown in FIG. 2, the side handle 24 is located forward of the mid-line 40 of the length of the housing 4, wherein the handle 24 gripping portion 32 has a length 82 spanning a substantial extent of the adjacent side wall height 86. As shown in FIG. 3, in a preferred embodiment, the side handle 24 extends from the side wall 16 at an angle 94 relative the generally planar alignment 38 of the adjacent side wall 16. Specifically, as shown in FIG. 3, the angle 94 of the extending handle 24 relative the characteristic plane 38 of the adjacent sidewall 16 is preferable disposed at an acute forward angle 98, such that the side handle 24 extends from the sidewall 16 at an angular direction toward the front end 20 and extending generally away from the rear end 22 and the rear handle 26.

This structure provides a device 2 with a gripping portion of the side handle 24 that is closer to the front (proximal) end 20 of the device 2 than the handle ends (28, 30) which are integrally attached to the side wall 16. According to this aspect of the invention, the body of the side handle 24 protrudes from the side wall 16 at a forward angle 94, whereby the distance between the side handle gripping portion 32 and the rear handle gripping portion 42 includes the major extent of the length 100 of the housing 4. Thus, the mid-point of the length between the gripping portions 102 resides in a middle region of the length 100 of the housing 4, as shown in FIGS. 3 and 4. The recess region 34 of the housing 4 is located adjacent the gripping portion 32 of the side handle 24, preferably having an inwardly sloping segment 104 of the side wall. In the preferred embodiment, both ends of the side handle 24 are secured to the sidewall 16 at the inwardly sloping area 104 of the sidewall 16, and the gripping portion 32 is positioned adjacent, and outward from, the bottom surface region 106 of the recess 34, as shown in FIGS. 2-4.

The combination of a generally planar sidewall 16 (i.e., a major extent of the side wall generally resides about a characteristic plane 38) with an inwardly-extending recess region 34, along with the angular displacement 94 of the handle 24 extending from the side wall 16, results in the gripping portion 32 of the side handle 24 being configured to be closely positioned relative the housing body such as shown in the Figures in which the handle grip is adjacent the characteristic plane of the side wall (FIG. 4). In the embodiment shown, the adjacent surface 108 of the gripping portion 32 of the side handle 24 is less than about three inches (less than about 7.5 cm) from the lower surface area 106 of the recess region 34 and is immediately adjacent (or at least partially resides below) the characteristic plane 38 of the side wall. This aspect of the invention provides a side grip that is close to the main body of the device 2 to facilitate manipulation and alignment of the device 2 when held by a user. When this device 2 is in use, therefore, the user is able to extend his or her arm while holding the side handle 24, so the user's body may be positioned behind the rear 22 of the device 2 to aim along the length 100 of the device 2.

The front, or proximal end 20, of the device 2 preferably includes a collimator light assembly such as is known in the art. The collimator assembly preferably comprises a collimator light 62 and an collimator adjustment mechanism 112 associated with the opening in the front 20 of the x-ray device body, which adjustably defines the area of the radiographic exposure. In the embodiment shown in the Figures, the light emitted from the collimator 62 is adjusted by manipulation of the adjustable collimator mechanism 112 located at the proximal end 20, which controls shutter panels (not shown) at the proximal end 20 of the housing 4, thereby providing an adjustable area of light emitted from the proximal end 20.

Figure 5:
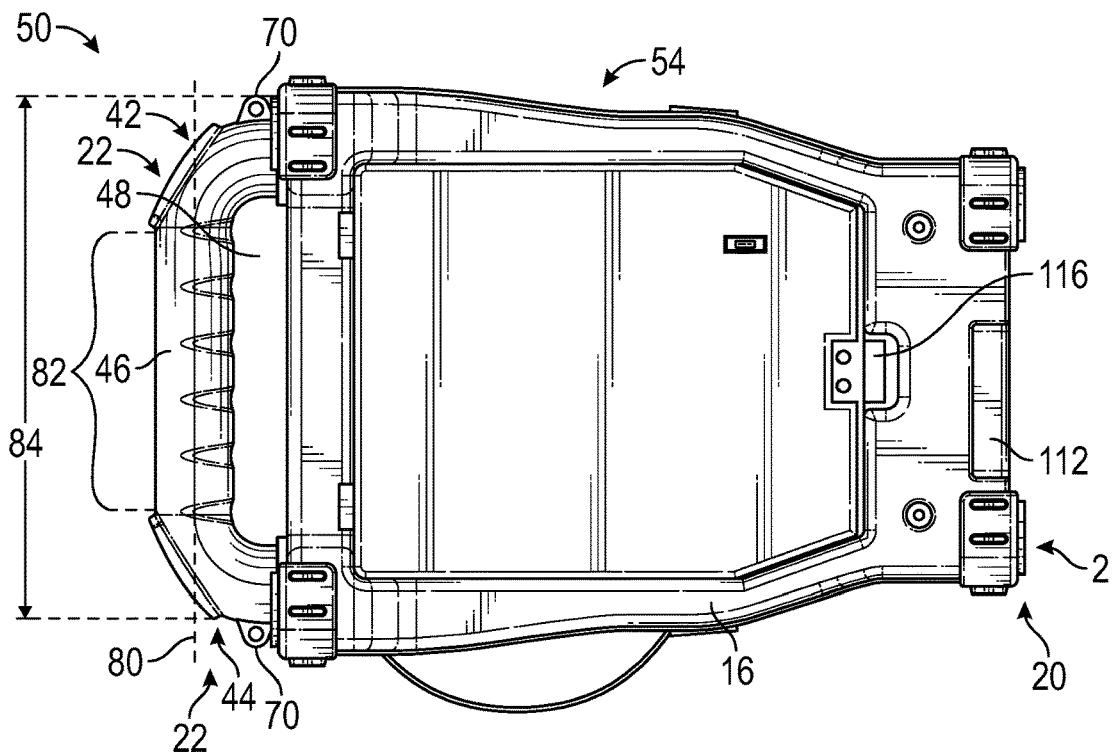
FIG. 5 is a side view of the device shown in FIG. 1, opposite the view of FIG. 2.
Figure 6:
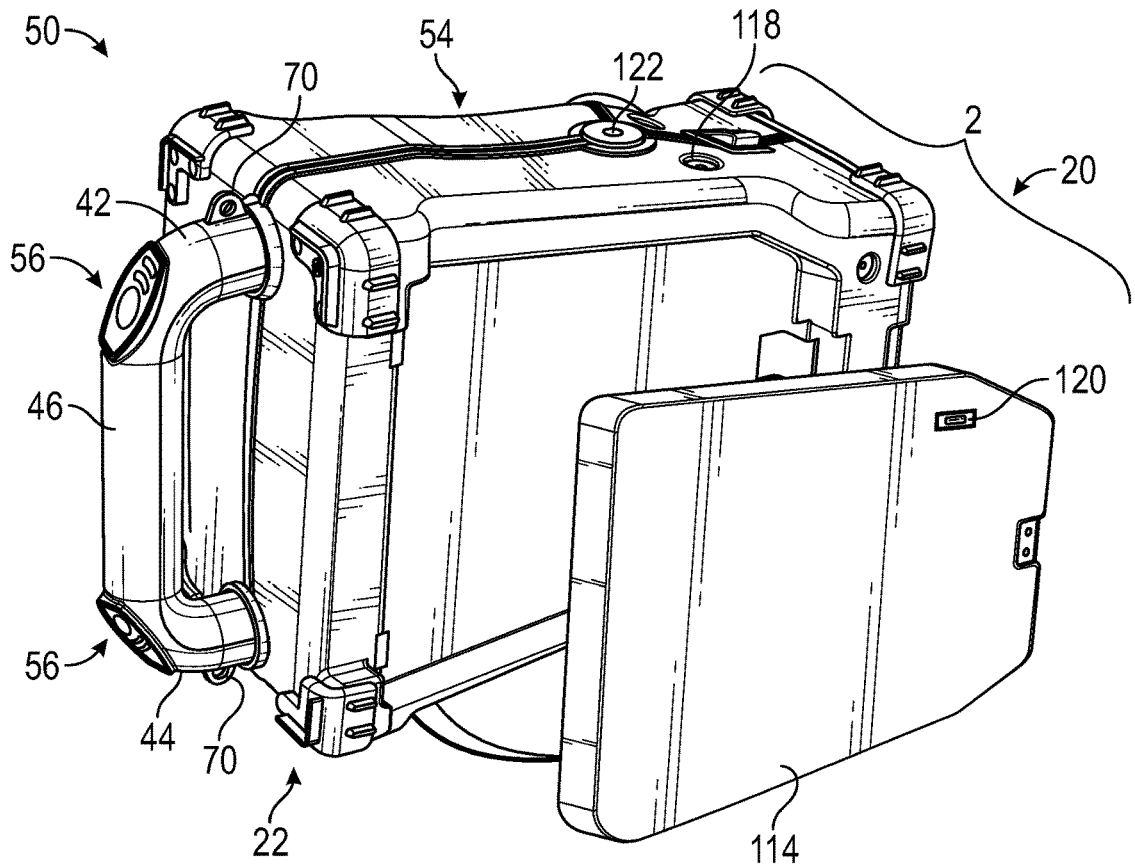
FIG. 6 is an elevated view of the device showing an exploded view of the removable battery secured adjacent the sidewall on the side shown in FIG. 5.

As shown in FIGS. 5-6, a battery 14 is provided, preferably as a removable battery secured in place by a securing mechanism 116 such as a spring-biased clip or other such fastener (such as a threaded fastener, a sliding mechanism or an outer casing). In the preferred form of the invention, the battery 114 is a rechargeable and removable battery secured to an outer wall of the housing 4 that is opposite the side wall 16 location of the side handle 24. The batter may be charged independently or may be charged by connection of a power source at a power plug 118. The power plug 118 may be configured such that, when connected to a power source, power is supplied for use of the device 2 while also charging the battery 114. The device 2 also preferably includes a battery power indicator 120, such as an LED light which indicated the residual charge of the battery 114 when pressed or otherwise activated by the user.

The portable device 2 also preferably includes a pair of support connectors 122 for attaching a large handle or for attaching the device 2 to a stand or boom (not shown). The support connectors 122 are preferably each a standard threaded receiver positioned on opposed outer side walls 16. Such threaded connectors may be of a common variety, such as that which is commonly used for portable x-ray devices for attaching a handle that straddles the width of the housing 4 to attach at each of opposed side walls, or for a u-shaped bracket attached to a stand or a boom. In the preferred embodiment, the side connectors 122 are located generally in the middle area along the length 100 of the housing 4, adjacent the side wall handle 24. In the preferred embodiment, such as shown in FIG. 3, the connectors 122 are positioned on opposite sides of the housing 4, located at or adjacent the midline 40 and adjacent the side handle 14, thus providing an attachment mechanism 122 of the device 2 which is locate at or near the center of the housing 4 and yet not obstructed by the angularly extending handle 24. Further, because the side wall handle 24 is positioned close to the side wall and is preferably attached directly with only one of the side walls, it is preferable for the support connectors 122 to not be located on the same side of the housing 4 as the side handle 24 instead preferably being on the two opposed sidewalls 16 that are adjacent the generally planar sidewall with the side handle 24.

Figure 10:
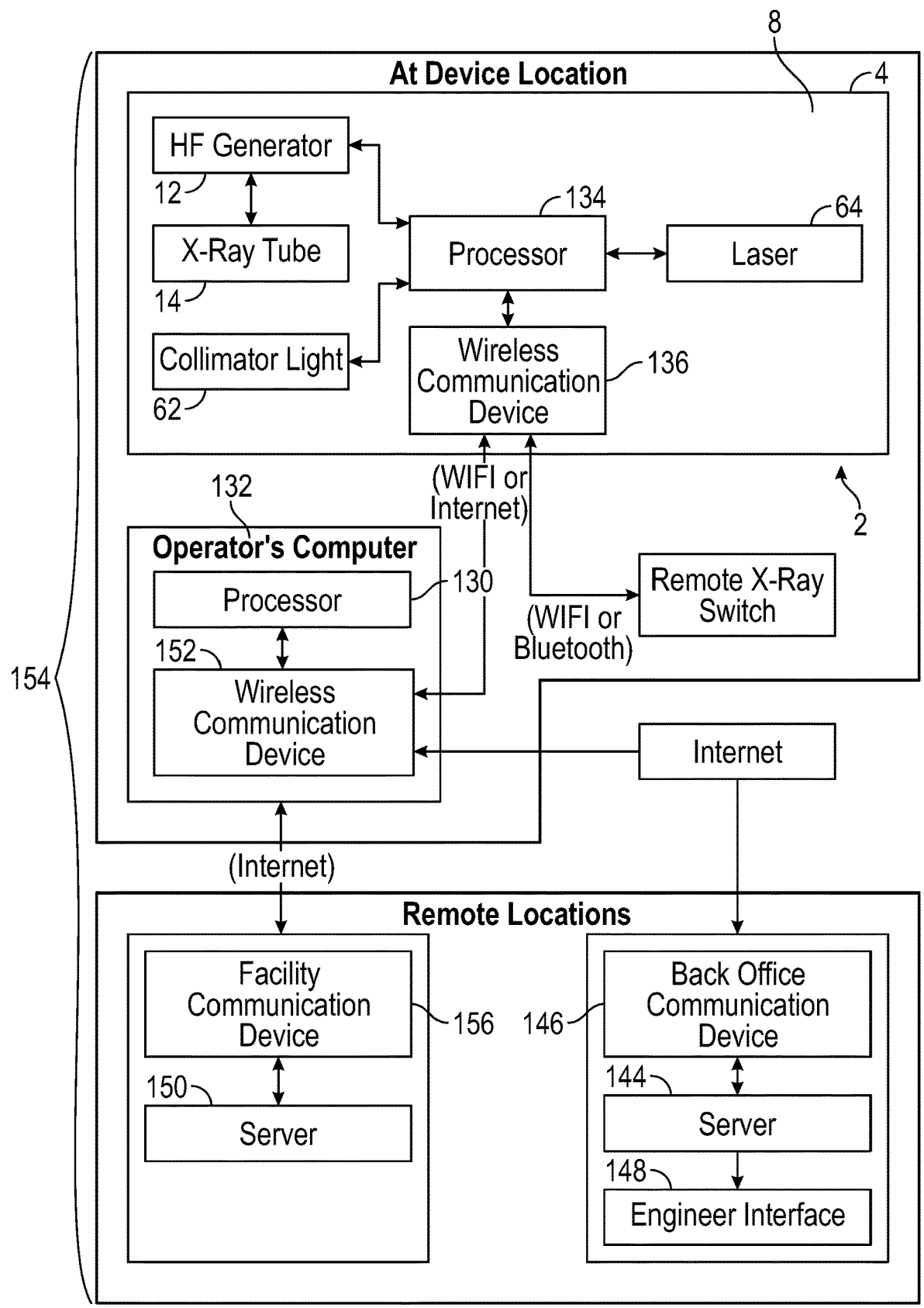
FIG. 10 is a block diagram identifying the device components and operating system of the present invention, including identification of the components and the structure and method for communication and operation of the device and the relative locations of the system according to the present invention; and, FIG. 11 is a block diagram identifying the device components and operating system of the present invention, including identification of the components and the structure and method for communication and operation of the device and the relative locations of the system according to the present invention.

As shown in FIGS. 10 and 11, the device 2 preferably is operated by a user through the combination of activation by the triggers 56 located on the handles (24, 26), and by communication between the device 2 and a processor 130 of a computer 132. In the preferred embodiment shown in the Figures, an internal processor 134 is in connected to a wireless communication device 136 such as a WIFI device, both located within the interior space 8 of the device 2. The operator uses an external computer 132 with an internal wireless communication device 152 (such as a WIFI communication device) configured to communicate with the hand held device 2 to perform setting functions for the device 2, which also may be used to receive images of the radiographic image. The device 2 (FIG. 7) preferably also is configured with electrical connection ports 140, such as an Ethernet cable connector 142, which is internally wired to the internal processer 134 to bypass the wireless communication, such as in the situation in which WIFI is riot available.

In operation, the user supports the device 2 by holding the two handles (24, 26) to align the target field for x-ray exposure. To facilitate proper alignment, the user pushes the trigger 56 on the side handle 24 to activate an alignment function of the device 2, such as illumination of the field by a light emitting from the collimator 62 at the proximal end 20. As described above, the side handle triggers 56 are configured to provide a trigger for the user to activate a collimator light 62 or to activate a laser 64 emitted from the front 20 of the device 2, such as cross-markings. This is done by simply pressing one of the side handle triggers 56 to a first position to illuminate the light 62 and then pressing the trigger to a second position to activate the laser 64 cross markings. The user then manipulates one of the triggers 56 of the rear handle 26 to activate the device 2 for x-ray exposure. In the preferred embodiment, this includes providing rear handle triggers 56 which, when pressed, activates an indicator light 66 a function of identifying the readiness of the x-ray and then also may be pressed to activate the radiographic exposure. As described above, this is preferably configured as a pair of triggers 56, each located at opposite sides of the gripping portion 46 of the rear handle 26, and each trigger 56 being a button which may be pressed to a first level for readiness of the device 2 and a second position for activating the x-ray exposure. Indicator lights 66 adjacent the trigger 56 are preferably electrically connected to receive a signal from the processor 134 to provide the operator an indication of the readiness of the device when the trigger is pushed to the first level.

The configuration of having an internal processor 134 in communication with the internal wireless device 136 also provides the ability for direct communication between the device 2 and a remote server 144 at a back office location, other than the processor 130 or computer 132 used for receiving the x-ray image. The device 2 is thereby configured such that the operator's computer 132 (a laptop or tablet computer) wirelessly communicates with the device 2 to control the x-ray generator 12 and the image system of the device 2, while the back office server 144 is in wireless communication with the device 2 to perform back office control functions, such as configuring, calibrating and trouble-shooting the functions of the device 2. More specifically, the wireless communication link with the back office server may be made through the Internet to: (1) check the general status of the systems within the device 2, to check the functions of the modules and subsystems, check the programmed configuration of the system, identify calibration status or calibration dates, identify the number of exams performed, update software, etc.; (2) identify errors such as by downloading error locks to assess what intervention is needed; (3) perform trouble-shooting functions; (4) alter or update the calibration of the functional system of the device 2; (5) upgrade software of the device 2; and, (6) upgrade or modify the anatomical programmer of the device 2 to assure optimal performance. Of course, most or all of these functions may involve a system engineer associated with the back office server, and the functions may be initiated by the back office server or engineer or may be initiated by the server within the device 2.

The wireless communication between internal components of the portable device 2 and the back office server 144 is configured to provide information to a service engineer and the ability for corrective measures by the service engineer, regardless of the location in which the portable device 2 has been taken, provided an Internet connection is available. This is particularly useful for hand-held portable devices of the present invention, which are designed to be taken where needed, such as where animals are kept. For example, the system 154 of the present invention, including a portable hand-held x-ray device 2 having an internal communication device 136 to transmit and receive signals to and from a back office server 144, provides remote access to the operating systems of the device 2 while it is being used at remote locations for generating x-ray's of horses. This avoids the need for an engineer to travel to the location or have the device 2 shipped to a technician. Unlike non-portable x-ray equipment which is kept at a particular location, a hand held portable device 2 such as that shown in the Figures, is not easily available for service or even routine maintenance. Thus, it is optimal to have a system 154 which includes a wireless communication device 136 and internal processor 134, within the hand held device 2, to communicate with devices at remote locations. This, for example, enables full access to the underlying programs and settings of the device 2 for manipulation by the back office server 144.

In a preferred embodiment, the communication link between the internal processor 134 of the portable device 2 and the back office server 144 includes wireless connection to an operators' computer 132 as a relay communication point between the device 2 and the back office communication device 146. This aspect of the system 154 is shown in FIG. 10, configured to provide communication connection of the device 2 to the back office through the operator's computer 132 at the location of the device 2. In this aspect of the system of the present invention, the portable x-ray device 2 has an internal processor 134 configured to send and receive signals to/from an external computer 132 through a communication device 136, and uses the operator's computer to receive signals and communicate the data to/from remote processors 144, 150. In the preferred embodiment of this system shown in FIG. 10, the communication device 152 of the operator's computer 132 is wirelessly connected to the x-ray device 2 and configured to wirelessly communicate with a back office communication device 146 and/or another facility communication device 156 at a remote locate relative the device 2 and the operator computer 132.

As shown in FIG. 10, this communication system is unique in that the functional components of the x-ray, most notably components 10 of the x-ray generator 12 (which also is capable of providing information regarding readiness and/or malfunction of the x-ray tube 14), as well as the ancillary components such as the collimator light assembly 62 and the laser device 64, may be connected through the internal processor component 134 to transmit signals to the back-office server 144. In this configuration, the functional components within the housing 4 of the portable device 2 may be monitored, and the parameters of at least some of those components may adjusted through signals delivered to the internal control processor 134 through the wireless communication device 136. In the preferred embodiment, the functional status of the x-ray tube 14 is provided indirectly by a signal from the generator 12 to the internal processor, such that a direct connective link between the x-ray tube 14 and the processor 134 is not necessary. Preferably, communication from the internal processor to a remote location is performed over the Internet, and all such communications are relayed to and from the internal processor through an internal wireless device within the housing 4. The wireless communication device 136 within the housing 4 which is used to communicate to the back office server 144 is preferably the same communication device 136 which is used to communicate to the operator's computer 132—thus the operator's processor 130 is utilized as a relay hub tor data communication between the device 2 and remote location processors (144, 150). It is notable that the wireless communication device 136 within the housing 4 may comprise two or more separate communication devices, such that at least some of the functions for use of the device 2 may be performed with communication to the operator's computer 132 via Bluetooth communication protocol, while communication of other functions (such as the communication to with the back room) may be via WIFI and transmittal through the Internet.

As shown in FIG. 11, the processor 134 receives signals from a number of the components of the device 2, such as the triggers 56, and the internal components within the interior space 6, and is capable of delivering signals to the components. The internal processor also is configured to receive signal regarding other components to which may or may not receive a return signal from the internal processor, such as receiving error or service messages from certain components (such as the light generating component or the laser generating component). The processor within the housing 4 thereby sends signals to the back office processor 144 via the wireless device 136 communicating with the proximate computer 132 of the operator, which includes information regarding the components of the device 2. The information received by the back office processor 144 may then be compared to pre-loaded information in a memory storage device at the remote location, including information regarding identification of the device and its components. Based on comparison of the information received and the pre-loaded information stored or transmitted to the back office processor 144, certain actions may be taken by the back office processor, such as transmitting a signal initiating a service call, indicating a replacement part to be delivered, or signal initiating an alteration of the operating parameters of the device 2. Alternatively, the information received by the back office processor 144 may be compiled or organized for delivery to a service engineer through an engineer interface 148 for action to be taken or transmitted to memory associated with the back office processor to log the information received.

In a preferred embodiment, as shown in FIG. 10, the high frequency generator 12 and the x-ray tube 14 are each in two-way communication with the processor within the housing 4, for exchange of signals relating to information transmitted to and from the external computer 132 and/or the back office server 144. The processor 134 also is configured be in electrical communication with the other components within the housing 4, such as the collimator light component 62 and the laser component 64. This electrical communication not only provides the functions of monitoring and servicing the components of the device 2 through the processor 134 receiving signal for such functions, it also is used for controlling the operation of the device 2 in use. This is done through the processor 134 receiving signals from the local computer 132 that are either generated on site at the computer by the operator, or by signals relayed from the back office processor 144 to the device 2, for adjustment of the components.

In the preferred embodiment, therefore, the portable x-ray device 2, and the operation thereof, according to the present invention is as follows: the x-ray device 2 is wirelessly connected (configured for communication of signals) to the operator's computer 132, which is in communication with sites over the Internet, and may also be connected with communication link directly with a processor 150 at the facility (e.g.: hospital or clinic) at or near the location of use. This may be advantageous because it is a configuration that utilizes the powerful communication device 152 of the operator's computer 132, rather than having to equip the portable x-ray device 2 with such a powerful wireless communication device. The operator's processor 130 and communication device 152 is preferably a computer, such as a laptop computer as identified in the Figures, but may also be a cell phone with the appropriate software for such function.

The present system, in which the portable x-ray device 2 has an internal processor 134 and a wireless communication device 136 that is in communication with a back office server 144 or processor (preferably through communication link with the operator's computer to then transmit signal through the Internet to the back office) provides access to remotely control aspects of the central components of the device, the X-ray generator 12 and image system. This allows remote access to such functions as though the service engineer were on site, at the location in which the device 2 is used. In a preferred form of this aspect of the invention, the service engineer interface 148, or a processor 144 pre-loaded with information for making adjustments to a device 2, may be used to perform the following processes on the device 2 remotely: (1) determine the status of the system (checking for errors to assure all of the modules and subsystems are working properly); (2) confirm the configuration of the system and suitability of the potential configuration options for the particular functions needed; (3) check the last calibration date and usage (number of exams performed, type of exams performed and at what level of power, etc.) and confirm the software and firmware version of the device 2; (4) download any error locks to review the type of failures the system has experienced and evaluate necessary intervention needed; (5) perform troubleshooting to identify and evaluate a problem in the system and thereby determine what spare part will be needed to solve the issue; (6) change the system configuration or personalizing the function of some options to optimize the performance of the system; (7) check the calibration of the system and recalibrate it if needed; or (8) upgrade and/or modify the Anatomical Programmer, to optimize the radiological techniques to obtain the best possible performance of the system.

The system of the present invention, therefore, provides a portable x-ray device 2 which houses a processor 134 that is configured to communicate to an operator computer 132 in close proximity to the device 2 for transfer information to and from the computer processor, as well as to and from a distant processor (144, 150) (by way of communication over the Internet or other network from the computer to a back office receiving system). According to this aspect of the invention, the operator's proximal computer 132 is configured to communicate information and commands for operating the portable device 2, and to also communicate commands and data from a back office server 144, or other remote server 150, which are located distant from the portable device 2. The local commands, (i.e., that which is generated by the operator) may include such operating parameters as the exposure time and other functions of the device 2 for the specific use as may directed by a technician using the device 2, while the distant commands (i.e., that which is generated from the back office) may be directed by an technician with the device supplier based on information received through the system.

As is shown in FIG. 11, in the preferred form of the invention, the x-ray high frequency voltage generator 12 is preferably configured to be in direct communication with the internal processor, which receives information from the component and provides signal to the component for establishing x-ray exposure parameters. Specifically, the processor 134 within the housing 4 is electronically connected to the x-ray generator 12, collimator light 62, laser generator 64 and the wireless communication device 136, and is configured to send signal to the indicator light 66 on the housing 4 and to receive signal from a trigger 56 of the handles (24, 26). The internal processor communicates through the wireless communication device 136 in the housing 4 to the operator computer 132 via wireless connection to a wireless device 152 associated with the computer 132, to relay signal between the portable device processor 134 and the computer processor 130. In the preferred embodiment, this operation mode of the system provides functional operation of activity and transmitting the x-ray function and image.

The system also provides a service, or trouble-shooting, mode by communication over the Internet with a remote processor 144, 150. In the preferred form of the invention the service mode of operation utilizes the communication link between the portable device 2 and the computer 132 to facilitate a relay of signals to/from the computer 132 with a remote server 144, 150, In a preferred embodiment, the system may be operated in either the operation mode or the service mode independently, or simultaneously.

It should be emphasized that the above-described embodiments, particularly, any "preferred" embodiments, are possible examples of implementations, merely set forth for a clear understanding of the principles of the invention. Variations and modifications may be made to the above-described embodiment(s) of the invention without substantially departing from the spirit and principles of the invention. All such modifications are intended to be included herein within the scope of this disclosure and protected by the following claims.

The invention is claimed as follows:

1. A portable x-ray device comprising:
   a housing having a housing wall arrangement defining an interior space, an x-ray generator and an x-ray tube being encased by the housing within the interior space, said housing having a side wall defined by a length of the housing wall arrangement, a front wall comprising a collimator and a collimator adjustment mechanism to adjustably define an area of radiographic exposure, and an opposing rear wall defined by a rear portion of the housing wall arrangement;
   a side handle having a first end integral with the side wall, a second end integral with said side wall, and a first gripping portion residing between the first and second ends of the side handle, the side handle being positioned in a front portion of the length of the housing wall arrangement;
   a rear handle having a first end integral with the rear wall, a second end integral with said rear wall, and a second gripping portion residing between the first and second ends of the rear handle;
   a first actuator trigger positioned adjacent the first end of one of either the side or rear handle, said first actuator trigger being configured to control a radiological function of the device; and
   a second actuator trigger positioned adjacent the second end of said either the side or rear handle, said first and second actuator triggers being positioned adjacent opposite ends of the gripping portion of said either the side or rear handle.

2. The portable x-ray device of claim 1, wherein said first and second actuator triggers are positioned on the rear handle, each said actuator trigger being configured to control said radiological function of the device.

3. The portable x-ray device of claim 2, further comprising:
   a third actuator trigger positioned adjacent said first end of the side handle and a fourth actuator trigger positioned adjacent said second end of the side handle, said third and fourth actuator triggers being configured to control a radiological function of the device.

4. The portable x-ray device of claim 3, wherein:
   said first and second actuator triggers of the rear handle are configured to provide a switch to initiate x-ray exposure and said third and fourth actuator triggers of the side handle are configured to provide control of a light emitted from the device to identify a target of an x-ray exposure.

5. The portable x-ray device of claim 3, wherein each of said actuator triggers comprise a button that is positioned at an end of the gripping portion of the handle such that a user may manipulate the button with the user's thumb when holding the handle.

6. The portable x-ray device of claim 3, wherein the side handle is located along a side of the device for a user to grip the side handle with one hand to support the device, and said rear handle is located at a position for a user to simultaneously grip the rear handle with the other hand to support the device, and said actuator triggers being positioned for the user to manipulate at least one trigger of each handle simultaneously while holding the device.

7. The portable x-ray device of claim 1, wherein the side of the housing has an indented region defining a void region adjacent the side handle, said void region providing a space for a user to fit a hand to hold the side handle.

8. The portable x-ray device of claim 1, wherein the housing has a side length with a central axis separating a front portion and a rear portion of the length, said rear wall having a rear central axis, said side handle being positioned in the front portion of the side, said rear handle being generally along said rear central axis.

9. The portable x-ray device of claim 1, wherein the housing has a length residing between a front and rear end, and said housing has a characteristic width, said side handle having a length along an axial line which spans across at least an extent of the housing side width.

10. The portable x-ray device of claim 9, wherein said rear wall of the housing has a characteristic height, said rear handle having a length along an axial line which spans across at least an extent of said rear characteristic height.

11. The portable x-ray device of claim 10, wherein the axial line of the side handle resides generally parallel the axial line of the rear handle.

12. A portable handheld x-ray device having a main body with a side wall defining a characteristic width of the body, a rear portion defining a characteristic height of the body, and an opposing front portion with a front wall comprising a collimator and a collimator adjustment mechanism to adjustably define an area of radiographic exposure, said main body having an inner space encasing an x-ray generator and x-ray tube and an exposure control processor, the portable handheld x-ray device further comprising:
  a side handle located adjacent to a front portion of said side wall and having a handle length extending across an extent of the side wall, said side handle having a first end and a second end with an intermediate gripping portion between said ends, said gripping portion being configured for a user to hold the side handle to support the device at a location adjacent the side wall;
  a rear handle located adjacent to a rear wall in the rear portion of the main body, said rear handle having a first end and a second end and an intermediate gripping portion between said ends, said gripping portion configured for a user to hold the rear handle to support the device at a location adjacent the rear wall;
  a first actuator trigger positioned on a first handle of either the side or rear handle, said actuator trigger being electrically connected to said exposure control processor to provide control for activation of a first function while the user holds the side and rear handles; and
  a second actuator trigger positioned on said first handle, said first and second actuator triggers being positioned adjacent opposing ends of the gripping portion of said first handle.

13. The portable handheld x-ray device of claim 12, wherein a second handle of said either the side or rear handle includes third and fourth actuator triggers, each positioned adjacent the gripping portion of said second handle and exposed to enable pressing by a user holding both handles, the actuator triggers of said second handle being configured to activate a second function of the device.

14. The portable handheld x-ray device of claim 13, wherein the actuator triggers of each handle are positioned in a configuration that allows a user to activate the first and second functions while holding the device with a hand on each handle.

15. The portable handheld x-ray device of claim 14, wherein at least one of said actuator triggers of the first handle is in a position for a user to activate said first function with a thumb of a hand holding said first handle, while at least one of said actuator triggers of the second handle is in a position for a user to activate said second function with a thumb of a hand holding said second handle.

16. The portable handheld x-ray device of claim 15, wherein each trigger of the second handle is configured with electrical connection to control a light emitting from a front portion of the device, and each trigger of the first handle is configured with electrical connection to activate x-ray exposure by the device.

17. The portable handheld x-ray device of claim 12, wherein the side handle is integral with the side wall and said rear handle is integral with the rear wall.

18. The portable handheld x-ray device of claim 17, wherein each of the first and second ends of the side handle is secured to the side wall, and each of said first and second ends of the rear handle is secured to the rear wall.

19. The portable handheld x-ray device of claim 12, wherein the housing has an indented portion adjacent the side handle to provide a void region for access for a user to grip the gripping portion of the side handle.

20. The portable handheld x-ray device of claim 12, wherein said main body has a body length between a front end and a rear end, said gripping portion of the side handle is positioned adjacent the front end of the main body and said rear handle extends beyond the main body.

21. The portable handheld x-ray device of claim 20, wherein the main body has a length with a midline at the center of the body, said side handle being located between the front end and said midline, and said rear handle being located at an extent away from the midline.

22. The portable handheld x-ray device of claim 12, wherein said main body has an overall length between a front end and a rear end, and the gripping portion of the side handle is located at a distance from the gripping portion of the rear handle, wherein said distance between said gripping portions is more than half of said body length.

23. The portable handheld x-ray device of claim 12, wherein a support strap connector is located adjacent each end of the side handle and each end of the rear handle.

24. A portable x-ray device having a main body with an elongated side wall arrangement and a rear wall, said body having an inner space encasing an x-ray generator and x-ray tube and a control processor, the device comprising:
  a side handle with an elongated first gripping portion positioned adjacent an extent of said side wall;
  a rear handle with an elongated second gripping portion positioned adjacent said rear wall;
  a pair of actuator triggers located at opposite ends of the gripping portion of either the side handle or rear handle, said actuator triggers each being configured as a switch for a user to control a function of the device while holding the device at said gripping portions of the side and rear handles; and
  a second pair of actuator triggers located at opposite ends of the gripping portion of the other of said either side or rear handle, each of said second pair of actuator triggers being configured as a switch for a user to control a function of the device while holding said gripping portions of the side and rear handles.

25. The portable x-ray device of claim 24, wherein the first pair of actuator triggers is located on the side handle and is configured to control a function of the device for defining an x-ray exposure area, and said second pair of actuator triggers is located on the rear handle and is configured to control activation of an x-ray exposure, such that a user may simultaneously operate both functions of the device while holding the device at both handles.

26. The portable x-ray device of claim 24, wherein said main body has a body length between the rear wall and a front end of the device, said side handle is located adjacent the front end of the device, and said rear handle extends beyond the main body.

27. The portable x-ray device of claim 26, wherein the side wall arrangement comprises a generally planar segment and an indented segment, said indented segment being located adjacent the front end of the device adjacent said side handle.

28. The portable x-ray device of claim 26, wherein the main body has a length with a midline at the center of the body, said side handle being located between the front end and said midline, and said rear handle is located at an extent away from the midline.

29. The portable x-ray device of claim 28, wherein the gripping portion of the side handle and the gripping portion of the rear handle are positioned at a separation distance, said separation distance being greater than half of said body length.

30. A portable handheld x-ray device, comprising:
a main body having a front end and a rear end;
a side handle having a gripping portion located adjacent said front end along a side of the main body, said gripping portion having an elongated extent along a first axis, and being configured for a user to hold the side gripping portion with a first hand while using the x-ray device;
a rear handle having a gripping portion located adjacent said rear end, said rear gripping portion having an elongated extent along a second axis, and configured for a user to hold the rear gripping portion with a second hand while using the x-ray device;
said side and rear gripping portions being positioned such that a user may hold and use the device while the side handle is on either the left side or the right side of the user; and
wherein at least one of said handles has an actuator trigger located at each end of the elongated extent of the gripping portion, each actuator trigger being configured to provide a switch for a user to control a function of the device while supporting the device by holding said gripping portions of the handles.

31. The portable handheld x-ray device of claim 30 wherein each actuator trigger comprises a button residing on a platform which is positioned at an angle relative to the axis of the gripping portion of said handle.

32. The portable handheld x-ray device of claim 30, wherein the actuator triggers are located on the side handle and configured to control a first function of the device, the device further comprising: a second pair of actuator triggers located on the rear handle and configured to control a second function of the device, each of said four actuator triggers comprising a button positioned at an angle relative to the axis of the gripping portion of the respective handle.

* * * * *